United States Patent [19]

Weissman

[11] Patent Number: 4,759,715

[45] Date of Patent: Jul. 26, 1988

[54] DENTAL PIN ASSEMBLY

[75] Inventor: Bernard Weissman, New York, N.Y.

[73] Assignee: IPCO Corporation, White Plains, N.Y.

[21] Appl. No.: 3,499

[22] Filed: Jan. 15, 1987

[51] Int. Cl.$^4$ .............................................. A61C 5/04
[52] U.S. Cl. .................................................. 433/225
[58] Field of Search ......................... 433/225; 226/127

[56] References Cited

U.S. PATENT DOCUMENTS

| | | | |
|---|---|---|---|
| 3,675,328 | 7/1972 | Weissman | 433/225 |
| 3,728,794 | 4/1973 | Edelman | 433/225 |
| 4,053,982 | 10/1977 | Weissman | 433/225 |
| 4,057,186 | 11/1977 | Hedger | 226/127 |
| 4,202,101 | 5/1980 | Weissman | 433/225 |
| 4,219,620 | 8/1980 | Carse | 433/225 |
| 4,380,433 | 4/1983 | Ellmann et al. | 433/225 |
| 4,595,376 | 6/1986 | Nordin | 433/225 |

FOREIGN PATENT DOCUMENTS 2143609  7/1984  United Kingdom ................ 433/225

Primary Examiner—Gene Mancene
Assistant Examiner—Adriene J. Lepiane
Attorney, Agent, or Firm—Helfgott & Karas

[57] ABSTRACT

A dental pin assembly including an elongated dental pin inserted within a magazine sleeve. The magazine sleeve is removably inserted into the distal end of a shank and locked in place. The shank in turn is driven by a handpiece or manual driver for rotation of the pin. The pin is a composite of a plurality of individual contiguous coaxial pin sections, each pin section having a threaded stem and an enlarged head. Adjacent pin sections are separated by reduced diameter throat portions which are frangible to permit separation of one pin section from the next upon insertion of the one pin section into an aperture in a tooth stub. As one pin section is sheared off upon insertion, the next adjacent pin section is ejected from the adapter to place it in operative position for subsequent insertion into another aperture in the tooth stub. In this manner only one pin section projects at a time and all of the throat portions can be of identical diameter.

40 Claims, 6 Drawing Sheets

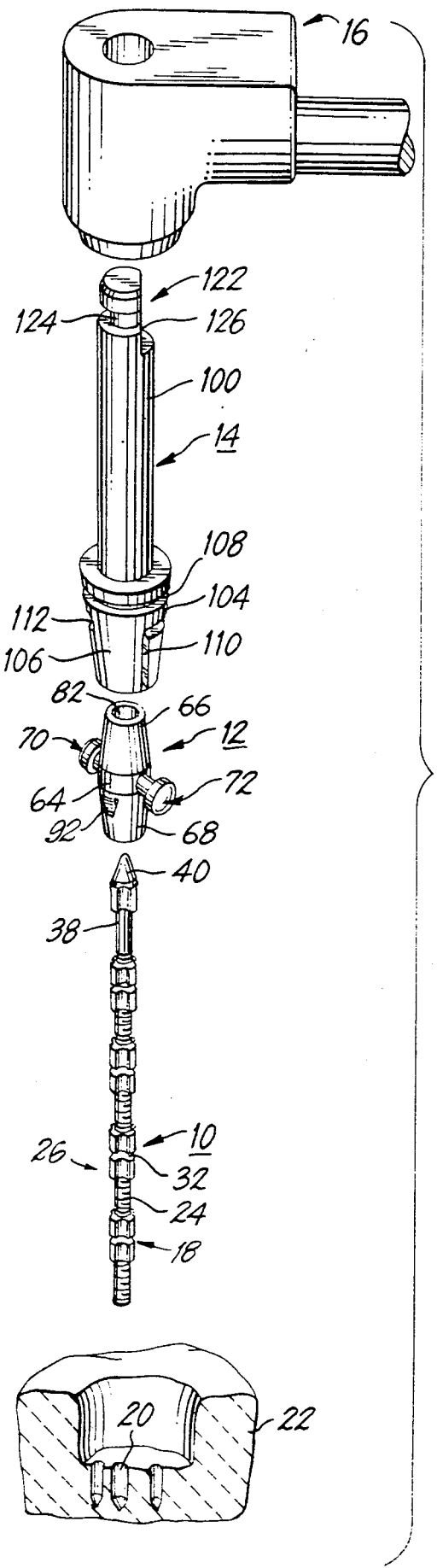
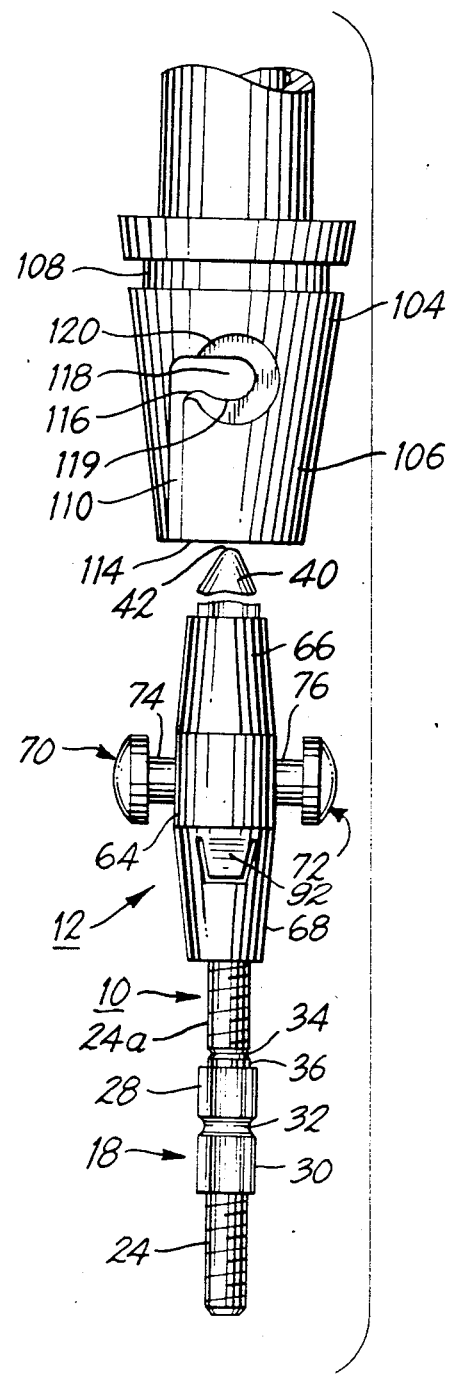
FIG. 1
FIG. 2

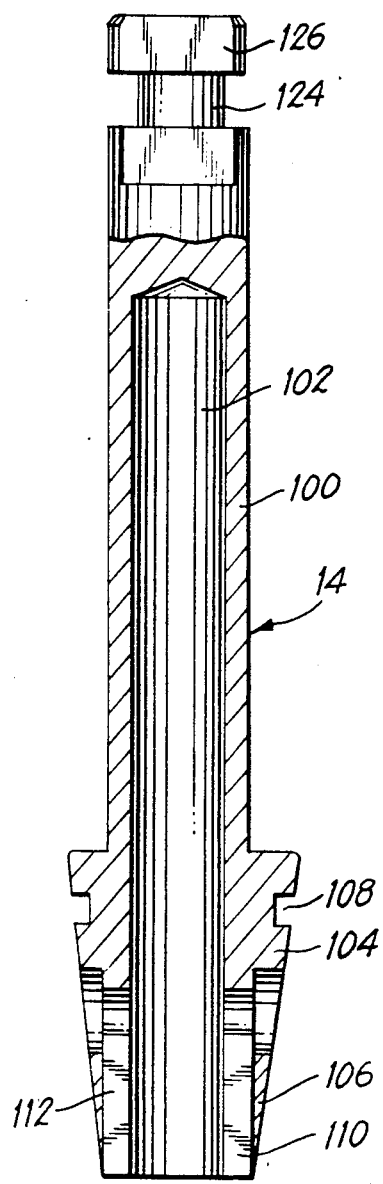
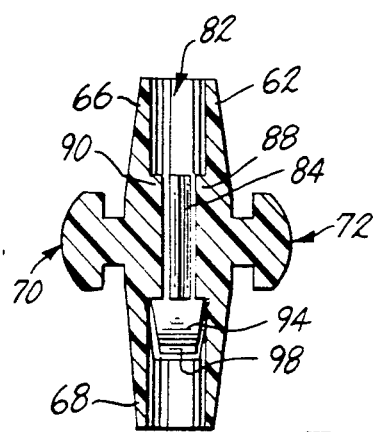
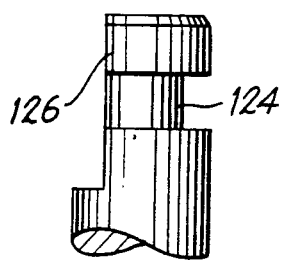
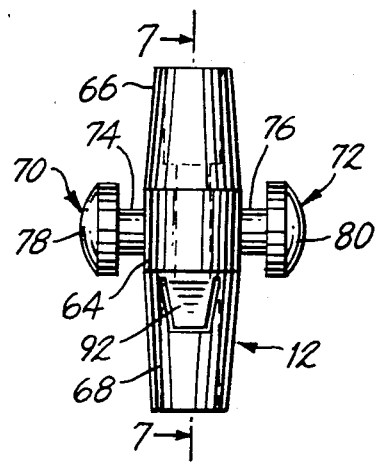
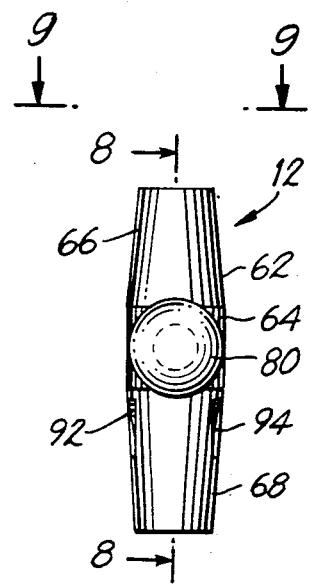
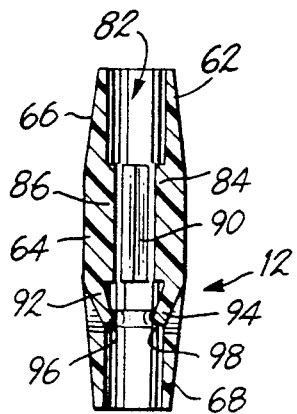
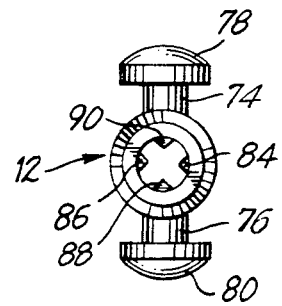

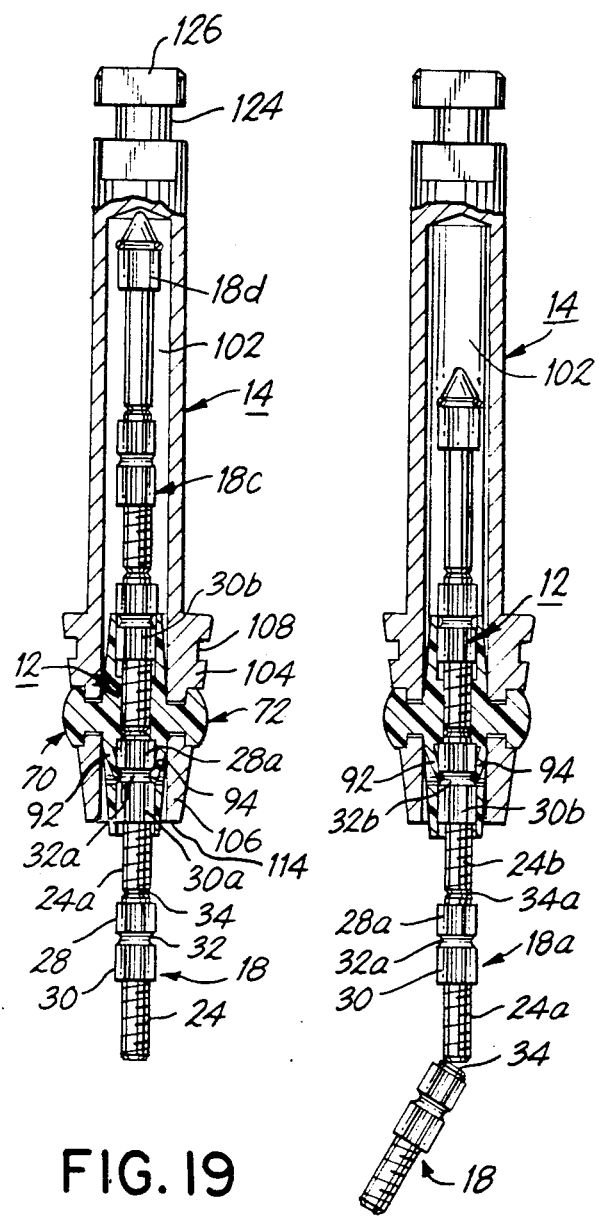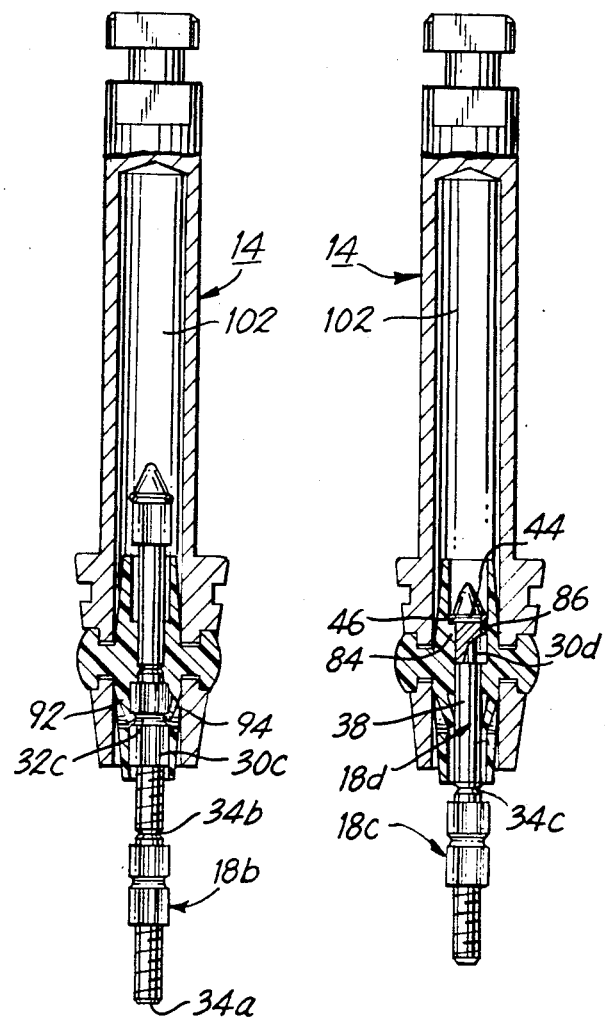
FIG. 19　　　　FIG. 21　FIG. 22
FIG. 20
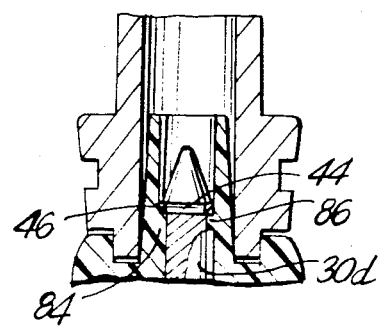
FIG. 22.A

DENTAL PIN ASSEMBLY

BACKGROUND OF THE INVENTION

This invention relates to dental pins, and more particularly to an elongated dental pin having a plurality of contiguous coaxial pin sections with each section sequentially moved into a projecting position from a magazine holder. The projecting pin shears off upon insertion into an aperture in the tooth stub and the next successive pin is projected.

In the formation of a dental superstructure onto a tooth stub, it is typical to insert one or more dental pins into the tooth stub with portions of the pins projecting upwardly from the surface of the tooth stub. The superstructure is then built up onto the tooth stub with the projecting portions of the pins used to aid in the retention of the superstructure onto the tooth stub. A number of such dental pins are often placed adjacent each other in order to aid in the retention of the superstructure.

An improved arrangement has been described in U.S. Pat. No. 3,675,328 assigned to the assignee of the present invention which describes an elongated dental pin having a plurality of individual threaded sections with each threaded section being separated from an adjacent section by a reduced diameter throat section. Each of the successive throat section are of increased diameter with respect to a proceeding throat section. The pin includes a single enlarged head. The head of the multiple sectioned dental pin is placed in a shank and the most remote threaded section is inserted into an aperture in a tooth stub. Upon reaching complete insertion, that remote section will shear from the remainder of the dental pin at its adjacent throat section. The next successive threaded section is then available for insertion in another aperture in the tooth stub. This next section will likewise shear at its adjacent throat section. Since the throat sections sequentially increase in size, the lowermost threaded section which is being inserted will shear before next two sections. The above described system is available from Whaldent International under the trademark TMS or Thread Made System.

An improvement in the multiple sectioned pin is described in U.S. Pat. No. 4,202,101. This patent relates to what is presently available from Whaldedent International under the trademark Link Series. In this structure, there is likewise provided multiple threaded sections with each section being separated from the next adjacent section by a reduced diameter throat portion. The respective diameters of the throats are successively increased in size to be sure that the lower most threaded section shears before the next adjacent subsequent section.

In the Link Series pin, the upper end which is inserted in the shank, includes a flattened tang with an arcuate outer edge to permit swaying of the pin within its receiving chamber. The sway facilitates insertion of the pin into the aperture and aids in the positioning of the pins.

In each of the above described systems, the pin itself comprises uniform threaded sections with the only discontinuity being the reduced diameter throat portions. Only a part of each of the threaded sections is inserted into the tooth stub while an upper part of each threaded section remains above the tooth stub for retention of the superstructure. Such upper parts can be bent or the entire pin can be angularly inserted in a tooth stub in order to provide an annular positioning of the upper projecting part to aid in the retention of the superstructure.

With the prior art pins, the entire pin with all its multiple sections projects from the shank and is retained within the shank by a single enlarged head portion at one end of the pin. Because all of the sections are always projecting from the shank, it is necessary to have the successive throats of increased diameter size to be sure that the lower most section will sever before the subsequent sections.

SUMMARY OF THE INVENTION

The present invention provides for an improvement in such type of dental pins. Specifically, it provides a dental pin which has a plurality of individual contiguous coaxial pin sections which are separated from each other by reduced diameter throat portions. However, all of the throat portions are of uniform diameter. The dental pin, however, is inserted within a retaining magazine sleeve which in turn is removably inserted into a shank which fits into the dental handpiece. The magazine sleeve is structured so that only one complete pin section will project at a time. The remaining pin sections are retained secured within the magazine and the shank which prevent other sections from shearing. In this way, the only pin section that can shear is the one projecting from the magazine, namely the lower most section. After such shearing off of the lower most pin section, the pin is axially moved within the magazine sleeve to eject the next successive pin section which is now available for insertion in another aperature in the tooth stub.

The magazine sleeve is preloaded with the elongated dental pin and is removably inserted into the distal end of a hollow shank. The opposing end of the shank is insertable either into a dental handpiece or a hand driver for rotational operation of the lower most pin section into an aperature in the tooth stub.

Each dental pin section includes a threaded pin with an enlarged head having a contoured shape. A mating contoured chamber is provided within the magazine sleeve for non-rotational securement of the pin within the magazine sleeve whereby the magazine sleeve with the pin secured therein are rotated by means of the shank. The magazine sleeve also includes one-way restriction means for permitting only outward axial ejection of the pin and preventing a back flow movement of the pin into the magazine sleeve. Color coding of the magazine sleeve can serve to identify the size of the pin contained within the magazine sleeve.

Utilizing a barrel shaped magazine sleeve with opposing tapered ends permits swaying of the magazine sleeve within the hollow of the shank to achieve the swaying benefit of the Link type pin heretofore described in the prior art. Likewise, the positioning of the upper end of the pin within the hollow of the shank with the hollow being a larger diameter than the outer peripheral diameter of the pin accommodates the swaying motion of the pin at its upper end.

Accordingly, it is an object of the present invention to provide an improved dental pin formed of multiple pin sections each of which can be sequentially inserted into respective aperatures in a tooth stub for building a superstructure onto the tooth stub.

Another object of the present invention is to provide an elongated dental pin having a plurality of coaxial pin sections with each pin section having a threaded post and an enlarged head, and each pin section is separated from the next pin section by a reduced diameter frangible throat portion for shearing of the pin sections from each other in succession.

A further object of the present invention is to provide an elongated dental pin having a plurality of pin sections with the pin sections separated from each other by a reduced diameter frangible throat portion, and wherein all of the throat portions are of identical diameter.

Another object of the present invention is to provide a dental pin system comprising an elongated dental pin having a plurality of dental pin sections coaxially connected to each other and positioned within a magazine sleeve for successively ejecting the pin sections to continuously provide a pin section operatively projecting from the magazine sleeve.

Yet a further object of the present invention is to provide a dental pin system having an elongated dental pin with multiple pin sections which sections can be sheared one from the next, the pin being inserted within a magazine sleeve and the magazine sleeve removably insertable into the distal end of a shank portion having a hollow interior chamber for accommodating the length of the dental pin.

Another object of the present invention is to provide a dental pin system having an elongated dental pin with a plurality of dental pin sections, each section being successively ejected from the distal end of a shank after shearing of a previous projecting pin section.

These and other objects, features and advantages of the invention will, in part, be pointed out with particularlity, and will, in part, become obvious from the following more detailed description of the invention, taken in conjunction with the accompanying drawings, which forms an integral part thereof.

BRIEF DESCRIPTION OF THE DRAWINGS

In the drawings:

FIG. 1 is a perspective exploded view of the various parts of the system in accordance with an embodiment of the present invention;

FIG. 2 is a an exploded view showing the pin inserted in the magazine sleeve with the adapter ready for insertion into the lower end of the shank;

FIG. 3 is an elevated, partially broken away cross sectional view taken through the shank;

FIG. 4 is a partially broken away view of the top end of the shank shown in FIG. 3 taken at right angles to the position shown in FIG. 3;

FIG. 5 is an elevational view of the magazine sleeve;

FIG. 6 is an end view of the magazine sleeve shown in FIG. 5;

FIG. 7 is a cross-sectional view taken along lines 7—7 of FIG. 5;

FIG. 8 is a cross-sectional view taken along lines 8—8 of FIG. 6;

FIG. 9 is a top view as indicated by lines 9—9 taken of the magazine sleeve shown in FIG. 6;

Figure 23:
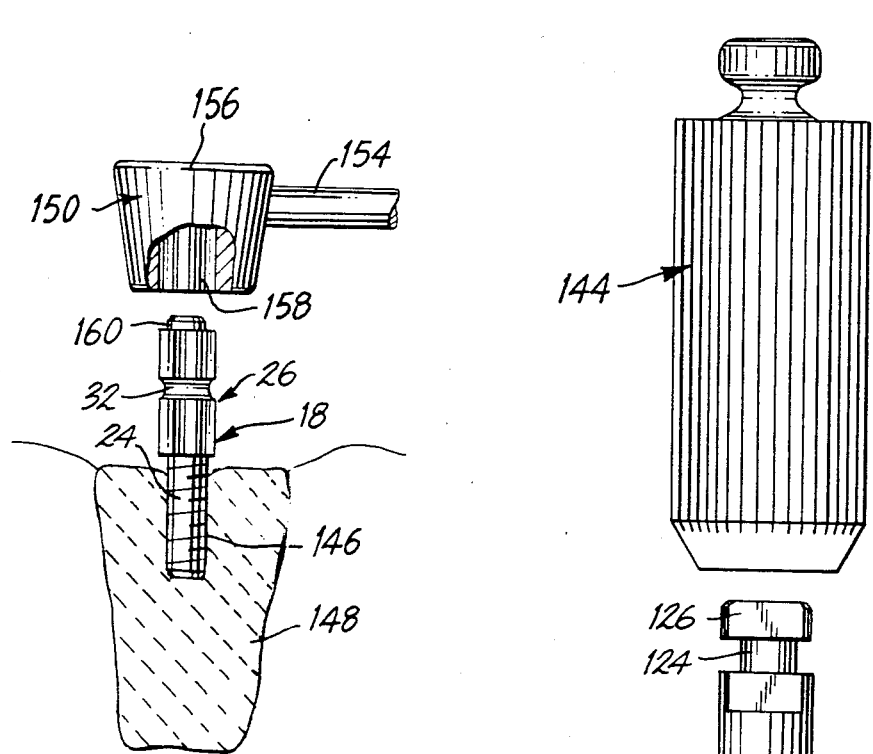
Figure 25:
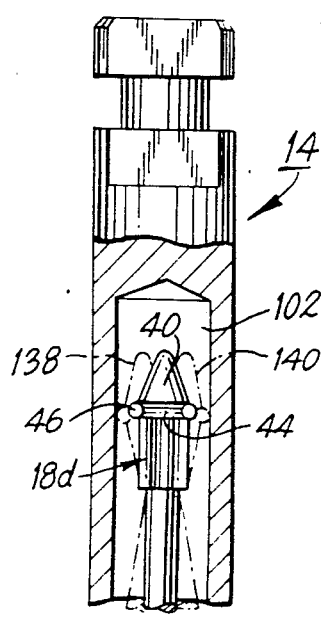
Figure 26:
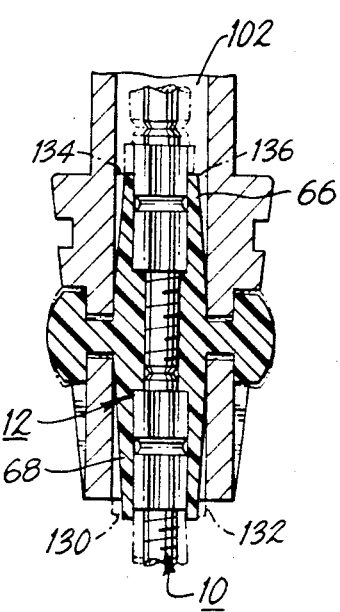
Figure 24:
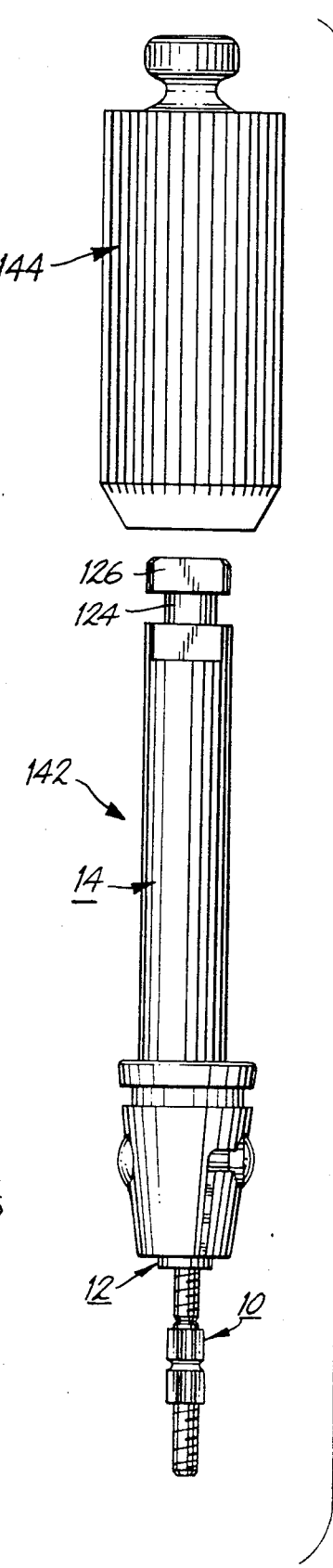
Figure 27:
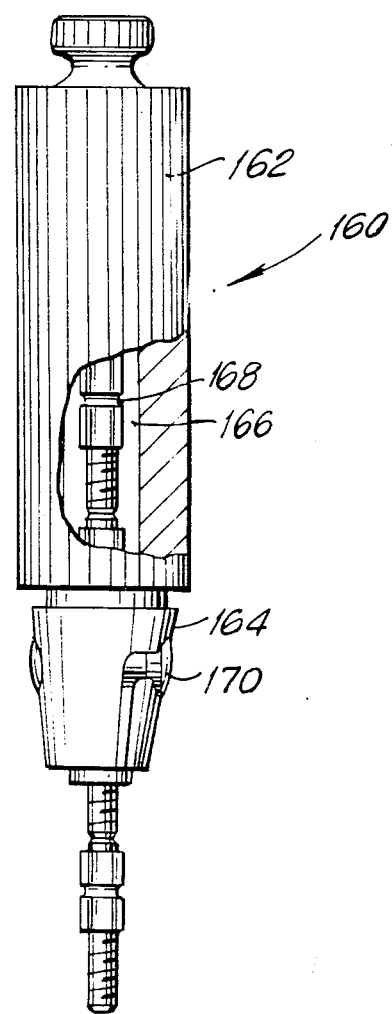

FIG. top view of another pin shape;

FIGS. 19–22 and 22A show various steps in the ejection of sequential pin sections with a new pin section continuously being projected from the distal end of the shank;

FIG. 23 shows the use of a manual adjusting tool for final adjustment of a dental pin section inserted within a tooth stub, utilizing the enlarged head for engagement by the manual tool;

FIG. 24 is an exploded view showing use of a hand driver for driving the shank;

FIG. 25 is a partially broken away cross sectional view of the upper end of the dental pin in the hollow chamber of the shank and showing the ability of the upper end of the pin to sway for achieving insertion of the pin into an aperature in the tooth stub;

FIG. 26 is an enlarged/cross sectional view showing the sway of the magazine sleeve within the hollow chamber of the shank for achieving insertion of a dental pin section in an aperature in the tooth stub; and FIG. 27 shows an elevational view of the magazine sleeve inserted into a combination shank and hand tool which can be reused with other magazine sleeves and pins.

In the various figures of the drawing like reference characters designate like parts.

DESCRIPTION OF THE PREFERRED EMBODIMENTS

The dental pin system of the present invention is shown in FIGS. 1 and 2. The pin system includes an elongated dental pin, shown generally at 10, a magazine sleeve adapter, shown generally at 12 and a shank portion, shown generally at 14. The shank portion 14 is adapted to fit either into a dental hand piece 16, as shown in FIG. 1 or into a hand driver, as shown in FIG. 24 and as will hereinafter be more fully explained. The dental pin 10 comprises a plurality of individual pin sections 18 with each section respectively fitting into a corresponding aperture 20 provided within a tooth stub 22. Each pin section 18 is threaded into its aperature and a dental superstructure will be then built up onto the tooth stub.

The dental pin 10 can best be seen in FIGS. 1 and 10–15. Each of the pin sections 18 includes a lower threaded post portion 24 which continues into an enlarged head portion 26. The head portion includes upper and lower parts 28, 30 separated by an annular groove 32.

Each pin section 18 is separated from the next adjacent pin section by a reduced diameter throat 34 which is frangible to permit separating one pin section from the next. To facilitate visibility of the frangible throat portion 34, an upper stem 36 is provided at the top of the head portion 26 which is connected to the throat portion 34.

Figure 10:
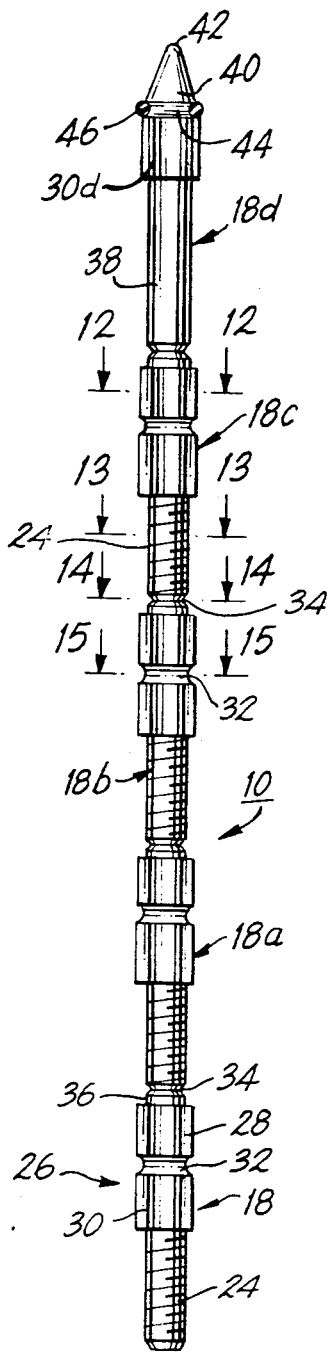
FIG. 10 is an elevational view of one embodiment of the dental pin in accordance with the present invention.

The dental pin shown in FIG. 10 includes five pin sections, identified as sections 18, 18a, 18b, 18c, and 18d. The upper most section 18d is distinguished from the other sections in various ways. It is noted that its stem portion 38 is unthreaded. Also, the stem portion 38 is slightly elongated more than the threaded stems of the other sections. The upper end 40 of section 18d is frustroconical in shape with the opposing sides tapered and terminating in a rounded dome shaped top 42. Within the annular groove 44 provided along the enlarged shaped head of the top section 18d, an O-ring 46 has been snapped in place.

The elongated pin shown in FIG. 10 is unique from those of the prior art in various ways. Firstly, it should be noted that all of the reduced diameter frangible throat portions 34 are of identical reduced diameter section. This is quite distinct from frangible dental pins of the prior art. In the prior art, since the entire pin with all of its sections continuously projects in its entirety from the distal end of the shank, in order to ensure that the lower most pin section will shear off before the next successive pin section, the throat portions get progressively larger. Thus, in prior art dental pins having multiple pin sections, the frangible throat portion of the lower most pin section has the smallest diameter with the next pin section having a slightly larger diameter. In the present pin, as shown in FIG. 10, on the contrary, all of the throat portions have the same identical diameter.

Additionally, in prior art dental pins with multiple pin sections severable from each other, the pin only included threaded portions without any enlarged head portion. The present pin has each pin section with not only a threaded portion but an enlarged head portion. The presence of an enlarged head portion on each pin section permits the head portion to serve as a stop for insertion of the threaded portion into the aperature in the tooth stub. Thus only the threaded portion will enter into the aperature. The head portion will remain seated on top of the aperture in the tooth stub and will be utilized for retention of the superstructure onto the tooth stub. Other benefits resulting from the presence of the enlarged head on each section will be explained hereafter.

Figure 11:
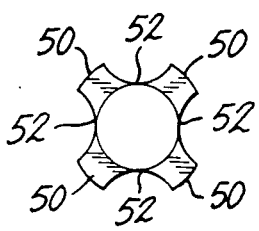
FIG. 11 is a top view of the pin shown in FIG. 10.
Figure 12:
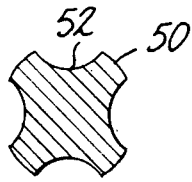
FIGS. 12–15 show respective cross sectional views of the pin shown in FIG. 10.
Figure 13:
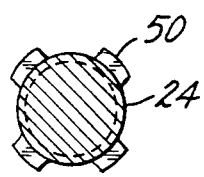
Figure 14:
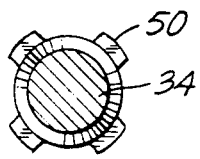
Figure 15:
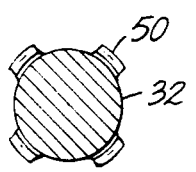

The cross sectional area of the enlarged head portion is best seen in FIG. 11 as being somewhat square having rounded corners 50 with inwardly arcuate opposing side portion 52. As shown in FIGS. 12-15, the annular groove portion 32 has a larger diameter than the threaded post portion 24 which in turn has a larger diameter than the throat portion 34.

Figure 16:
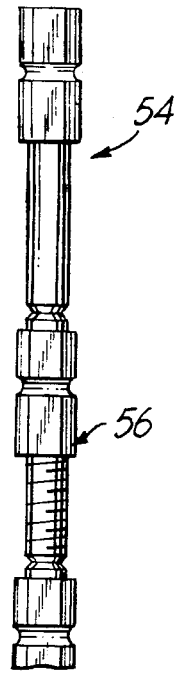
FIG. 16 is a partial elevational view showing a dental pin in accordance with another embodiment of the present invention.
Figure 17:
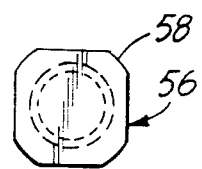
FIG. 17 is a top view of the pin shown in FIG. 16.

In addition to the particular shape shown in FIGS. 11-15, it is possible to form the post with enlarged heads having other shapes. By way of example, as shown in FIGS. 16 and 17, the post 54 of substantially similar configuration to that shown in FIG. 10 has an enlarged head portion 56 with a cross sectional area of a square having angled corners 58. The other portions of the pin of FIG. 16 would be substantially identical to that of FIG. 10.

Figure 18:
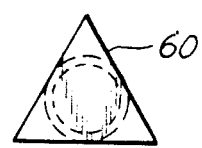

Other shapes of the head portions could also be utilized. For example, FIG. 18 shows a shaped head 60 in the form of a triangle. It should be appreciated, that the shape of the head of the pin sections is such as to permit engagement with a correspondingly contoured cavity is the magazine sleeve to prevent rotation between the head and the magazine. Therefore, various unique shapes or a flattened side could suffice to provide such non-rotational engagement between the pin and the magazine sleeve.

The magazine sleeve 12 of FIG. 1 can also be viewed in FIG. 2 and FIGS. 5-9. The sleeve 12 is shown to be in the shape of an elongated barrel 62 having a central cylindrical section 64 with an upper frustroconical tapered end 66 and a lower frustroconical tapered end 68. Projecting from the center cylindrical section 64 are diametrically opposed knobs 70, 72 each of which projects from a stem 74, 76 and terminates in an enlarged head 78, 80 having a rounded outer surface. Internally of the barrel is a passageway 82 through which the pin can axially pass. Longitudinally spaced along the passageway, approximate a center portion thereof, are a pair of opposing inwardly projecting arcuate ribs 84, 86 and 88, 90. These ribs provide the mating contour shape to the enlarged head of the pin sections. The mating contour provided by these ribs will permit axial movement of the pin within the passageway 82 but will prevent rotational movement of the pin within the magazine sleeve 12.

Inwardly struck into the bottom portion 68 of the sleeve are a pair of opposing tabs 92, 94 at the distal ends of which are internally projecting arcuate ribs 96, 98. As will hereinafter be explained, the inwardly extending tabs 92, 94 serve as one way controls permitting only forward projection of the pin within the sleeve while preventing reverse movement. The ribs 96, 98 engage within the annular groove 32 at the mid section of the enlarged head of each pin section for index advancement of the pin sections within the magazine sleeve.

The shank 14 can best be seen in FIGS. 1-4. The shank portion includes an elongated hollow barrel 100 including an interior chamber 102. The lower end of the shank is thickened at 104 and includes a forward tapered front end 106. Thickening of the front end provides additional strength for retaining the magazine sleeve, as will hereinafter be described. A peripheral channel 108 is provided for a finger grip to aid in grasping of the shank.

A pair of inverted L-shaped slots 110, 112 extend from the lower distal end 114 of the shank upwardly part way along its front thickened end 106. The L-shaped slots have a restricted neck 116 at the entrance to the horizontal leg 118. The end of the horizontal leg 118 sits in a counter-sunk groove 120.

At the upper end of the shank, there is provided a standard lock 122 for securement with a hand piece 16. Specifically there is provided an undercut neck 124 and one flat side 126 for driving engagement by the handpiece. The type of locking arrangement 122 is standard for handpieces.

The assembly of the dental pin system heretofore described can best be seen with respect to FIG. 2. Initially, the elongated pin 10 is preloaded into the magazine sleeve 12 such that the lower most pin section 18 projects from the lower end of the magazine sleeve 12 and the frangible throat portion 34 extends beyond the lower edge. This means that at least a portion of the next adjacent pin section, and specifically a portion of the threaded post 24A will have to project a bit. However, only one complete pin section projects from the magazine sleeve 12.

The magazine sleeve 12 is then inserted into the lower end of the shank 14 by sliding the opposing knobs, 70, 72 upwardly into the opposing slots 110, 112. When the stems 74, 76 reach the top, the magazine sleeve is twist locked into place in the lower end of the shank. The constricted portion 116 is narrower than the diameter of the stem 74, 76 of the knobs requiring a force twist in order to overcome the constriction. Once past the constriction, the stems will fit in place in the horizontal leg. To insure its retention, depressions 119 can be formed at the bottom of the horizontal legs to secure the stem in place. With the stems so positioned, the enlarged heads, 78, 80 of the knobs will sit into the countersunk grooves 120. The knobs are of a size large enough to project beyond the periphery of the shank in order to be able to grasp the knobs in twisting the magazine sleeve into place and also for subsequently releasing and removing the magazine sleeve from the shank.

With the pin preassembled into the magazine sleeve, and with the magazine sleeve loaded into the shank, the assembly will be ready for operation as is shown in FIG. 19. In the initial position, the distal most pin section 18 projects in its entirety from the end 114 of the shank 14. The reduced diameter frangible throat 34 also projects beyond the shank as does a portion 24A of the next adjacent pin section. The head portions 28A and 30A of the next adjacent pin section 18A is securely retained in the magazine sleeve 12 being positioned in the correspondingly contoured chamber contained therein. The inwardly struck tabs 92, 94 have their projecting ribs 196, 198 positioned within the annular groove 32A of the pin section 18A. A portion 30B of the further pin section 18B is somewhat disposed within the magazine sleeve. The upper pin section 18C and the upper most driver 18D are within the hollow chamber 102 in the shank and have freedom to pivot and sway within that chamber 102 since the size of the chamber is larger than the peripheral size of the pin sections.

With the pin assembly as in FIG. 19, the shank would be loaded into a handpiece as in FIG. 1 for automatic rotation of the lower most pin section, or placed within a hand driver, as in FIG. 24, for manual rotation. The lower most pin section 18 will be threaded into an aperture in the tooth stub. As the pin bottoms out, it will shear along the frangible throat portion 34, as shown in FIG. 20. The lower most section 18 will then remain in the tooth aperature for final adjustment, as will hereinafter be explained.

As the lowermost section 18 approaches the bottom of the aperture, the user can pull up on the shank 14 so that the elongated composite pin 10 will be axially drawn through the magazine sleeve 12 until the next adjacent pin section 18A is now projecting from the shank portion as shown in FIG. 20.

The inwardly directed tabs 92, 94 will slide over the thinner diameter threaded post 24B and the next adjacent head portion 30B until it engages the annular groove 32B and will catch the groove providing an indexed stop for the proper positioning of the pin in its next successive location.

The tabs 92, 94 will pivot so that by pulling upward on the shank or pulling forward on the dental pin, the dental pin can move outwardly from the shank. However, because of their downwardly and inwardly angled oriertation, the tabs will prevent a backward movement of the dental pin to prevent the dental pin from sliding back into the shank. This is important since it prevents slippage of the dental pin during actual threading of the pin into an aperture.

The process continues with the section 24A shearing off at the frangible throat portion 34A at which time the next adjacent pin section 18B will be projecting from the shank. At that time, the head portions 30C and 32C of the section 18C will be driving the rotation and the tabs 92, 94 will be engaged within the annular groove 32C.

After the section 18B is sheared off at the frangible throat 34B, the final section 18C is projecting from the distal end of the shank as shown in FIG. 22. The driver 18D is now the driver for driving the pin section 18C.

The final driving section 18D includes an O-ring 46 in its annular groove 44. The O-ring has an outer dimension which projects beyond the peripheral dimension of the pin. As such, as it enters into the contoured chamber within the magazine sleeve, it will abut the ribs 84, 86, 88, and 90 and will prevent the final section 18D from being pulled through the sleeve, as shown in the enlargement view of FIG. 22A. The lower part of the head portion, 30G will, however, be received within the contoured chamber of the magazine sleeve and will be engaged by the contoured chamber to drive the lowermost pin section 18C. In order to be sure that the entire pin section 18C with the frangible throat 34C projects beyond the distal end of the shank, the uppermost stem 38 can be made longer than the other threaded portions 24. This will accommodate the fact that the O-ring prevents the entire head from lowering the same extent that the other enlarged heads were lowered for each of the other pin sections.

It should be appreciated that the O-ring also prevents falling out of the entire pin so that there is no danger of having the pin ever slide through the entire sleeve and fall into a patient's mouth during use. Likewise, the twist lock arrangement between the magazine sleeve and the shank as well as the constriction at the entry into the horizontal leg of the twist lock arrangement, prevents the magazine sleeve from any possibility of sliding out from the shank.

One of the unique benefits of the Link Pin System as was described in the aforementioned U.S. Pat. No. 4,202,101, is its ability to sway or pivot. Such sway is also provided in the present system as shown in FIGS. 25 and 26. The magazine sleeve 12 has its lower portion 68 and its upper portion 66 frustroconically tapered. This permits a sway or pivoting of the magazine sleeve 12 within the chamber 102 in the shank 14. Such sway is shown in dotted lines at 130, 132 at the bottom portion and 134, 136 at the top portion. The upper end 18D of the pin section can likewise sway within the hollow chamber 102 in the shank as shown by the dotted lines 138, 140.

As heretofore described, and as shown in FIG. 24, the dental pin assembly 142 including the shank 14 with the magazine sleeve 12 and the pin 10 can be placed within a hand driver 144 for manual rotation of the threaded pin sections into their respective apertures in a tooth stub. Such dental hand drivers were described in the aforementioned U.S. Pat. No. 4,202,101. A coupling arrangement could be included within the hand driver 144 to engage the flat section 126 and reduced diameter section 124 of the shank 14 to provide rotational engagement of the shank and also to permit the pivot and sway of the shank within the hand driver.

One of the benefits of the present elongated pin is that in addition to having a plurality of threaded sections which are separated by frangible throat portions, each of the sections include its own enlarged head portion. In such construction, as shown in FIG. 23, the lower threaded portion 24 will be positioned within an aperture 146 in a tooth stub 148. However, the enlarged head portion 26 will project above the surface of the tooth stub and will be available for retention within the superstructure. The annular groove 32 which is used for indexing during operational insertion of the dental sections also provides additional aid in retaining the superstructure onto the tooth stub.

An additional benefit to the presence of the enlarged head is that it permits the use of a manual tool 150 for final adjustment of the pin section on the tooth stub. The manual tool 150 can include a handle 154 and a head portion 156 within which there is provided an internal socket 158 having a contour matching the head 26 on the pin section 18. This tool permits final adjustment by placing the socket onto the enlarged head and rotating the tool 150. Often it may be desired to backoff the pin a few turns after it has been seated. Such adjustment can be manually achieved through the tool 150 using the enlarged head on the pin section.

As shown in FIG. 27, the magazine sleeve could be placed directly into a tool 160 which is a combination shank and hand drive. The upper part 162 has serrations to permit easy hand grip of the tool. The lower part 164 is similar to the end of the shank shown in FIG. 24. Internally, there is provided an internal base 166 for receiving the pin 168 held by the magazine sleeve 170.

The annular grooves 32 in the pin provide for other benefits in addition to those previously mentioned. Specifically, in addition to aiding in the retention of the superstructure, and in addition to playing an integral part in the one way ratchet engagement of the tabs into the grooves, it can also serve to snap fit a ring such as a C-ring or O-ring to enlarge the head. It can also be used to tie together a number of adjacent pins in a network arrangement on the tooth stub.

Typically, the magazine sleeve will be formed of a soft plastic material and can be colored to define the size of the pin contained therein. The shank can be colorless and can be metal, hard plastic, or the like.

The O-ring 46 in the top groove 44 of the dental pin serves as a stop preventing complete ejection of the pin. Also, as shown in FIG. 25, it serves as a bumper to limit the sway at the upper end of the dental pin within the shank.

With prior pins that sheared, the pins only included threaded portions. If an enlarged head was desired on a pin, it was necessary to have a separate individual pin. The use of such of such separate individual pins required a manipulating end at the top of the pin which would be discarded after the threaded part of the pin was inserted. This required a great waste of material, especially when pins are made of precious metal. In the present arrangement, the benefits of both types of pins are achieved. Firstly, the pins are each provided with an enlarged head. At the same time, there is no discarded manipulating end for each of the pins. There is only one manipulating end for all four pins, since each of the pins serves as a manipulating portion for the next pin section.

Although the one-way ratchet arrangement was shown as including a pair of opposing tabs with ribs at the distal ends which engage the annular groove in the enlarged head, other types of one-way ratchet arrangements could be provided. The one-way ratchet arrangement also provides an indexing arrangement for the pins to insure progression of one pin after the other as they are ejected from the shank. Peripheral ribs could be provided within the magazine sleeve which would engage the annular grooves in the enlarged head portion of each pin section. The ribs could be rounded or pointed. These ribs will not engage any other portion but the annular grooves. Either the width of the rib could be made too wide for engaging the threads or the frangible throat portion, or else the diameter of the threads and frangible throat portion can be made smaller than the diameter of the ribs.

Although the enlarged head portions have been shown as smooth, these could also be threaded. The pin itself can be formed in various ways. However, it has been found beneficial to coin the entire pin thereby reducing the amount of waste material in the formation of the pin. This is of significance when the pin is made of precious metal.

Of significance is the fact that all of the frangible neck portions are of the same size throughout. This is contrary to prior art pins whereby the shear groove is of different depths to be sure that the lowermost portion shears first.

It will be noted that the frangible throat portion 34 on the pin sections is formed on top of a slight neck portion as can best be shown at 160 in FIG. 23. This neck portion could be eliminated and the throat could be formed at the upper end of the enlarged head.

There has been disclosed heretofore the best embodiment of the invention presently contemplated. However, it is to be understood that various changes and modifications may be made thereto without departing from the spirit of the invention.

What is claimed is:

1. An elongated dental pin for use in the retention of a superstructure onto a tooth stub, comprising a plurality of individual contiguous coaxial pin sections, each pin section comprising a helical threaded portion at its lower end and an enlarged shaped head at its upper end, adjacent pin sections joined by a reduced diameter throat section to permit self-shearing of each successive lowermost pin section from the remainder of the dental pin upon rotational insertion of the pin into the tooth stub, and wherein all said throat sections are of the same diameter.

2. A dental pin as in claim 1, and further comprising a stop means associated with the uppermost section for restraining the uppermost pin section from ejection from a holder.

3. A dental pin as in claim 2, and comprising an annular groove formed about the uppermost enlarged head, and an O-ring positioned in said annular groove and projecting beyond the periphery of said enlarged head.

4. A dental pin as in claim 1, wherein said enlarged head comprises a gripping surface for engaging a matingly shaped cavity in a retainer holder.

5. A dental pin as in claim 4, wherein the cross sectional shape of the enlarged head is a circle having opposing pairs of arcuate cut ins.

6. A dental pin as in claim 4, wherein the gripping surface comprises at least one flat surface.

7. A dental pin as in claim 1, comprising a tapered top end on the uppermost pin section.

8. A dental pin as in claim 1, wherein the dental pin is coined to form its shape.

9. An elongated dental pin for use in the retention of a superstructure onto a tooth stub, comprising a plurality of individual contiguous coaxial pin sections, each pin section comprising a spiral threaded portion at its lower end and an enlarged shaped head at its upper end, adjacent pin sections joined by a reduced diameter throat section to permit shearing of each successive lowermost pin section from the remainder of the dental pin, and further comprising an annular groove formed along each enlarged head for sequential indexing of the dental pin through a retaining adapter.

10. A dental pin as in claim 9, wherein the diameter of the pin at annular groove is greater than the diameter of the threaded portions which in turn is greater than the diameter of the pin at the throat sections.

11. A dental pin system comprising a dental pin having a plurality of contiguous coaxial pin sections each pin section comprising a stem, an enlarged shaped head, and helical threads about the stem for rotational threading of the pin, each pin section separated from the adjacent pin section by a reduced diameter throat portion to permit successive shearing off of the sections for sequential rotational insertion of the pin sections into respective apertures in a tooth stub, and a magazine sleeve retaining the dental pin such that only one complete pin section projects from the magazine sleeve at a time, and comprising ejecting means for sequential axial ejection of the next successive pin section as each pin section is rotationally sheared off.

12. A dental pin system as in claim 11, and comprising means for providing one way movement of the dental pin through the magazine sleeve.

13. The dental pin system as in claim 11, wherein the interior of the magazine sleeve has a matingly shaped chamber for permitting relative axial movement between the pin sections and magazine sleeve while preventing rotational movement therebetween.

14. A dental pin system as in claim 13, and comprising stop means on the uppermost enlarged head for preventing ejection of the uppermost pin section from the magazine sleeve.

15. A dental pin system as in claim 14, wherein said stop means comprises means projecting beyond the periphery of the uppermost enlarged head for preventing passage thereof through said matingly shaped chamber.

16. A dental pin system as in claim 13, wherein said magazine sleeve comprises an elongated barrel member having an internal axial passageway through which the pin is ejected, said chamber forming at least a part said passage way.

17. A dental pin system as in claim 16, wherein the upper and lower portions of said barrel are tapered toward their respective distal ends.

18. A dental pin system as in claim 16, and comprising a pair of diametrically opposed knobs projecting from said barrel to facilitate insertion of the barrel into a shank member.

19. A dental pin system as in claim 18, wherein said knobs are color coded to identify the size of the dental pin retained within the magazine.

20. A dental pin system as in claim 16, wherein the length of the barrel can receive the enlarged head of one pin section, and at least a portion of the enlarged head of the next successive pin section.

21. A dental pin system as in claim 16, and comprising a diametrically opposed pair of inwardly directed tabs struct from the barrel and extending into said passageway to engage the enlarged heads of the pin sections to provide one way axial movement of the pin sections through the passageway.

22. A dental pin system comprising a dental pin having a plurality of contiguous coaxial pin sections each separated from the adjacent pin section by a reduced diameter throat portion to permit successive shearing off of the sections for sequential insertion of the pin sections into respective apertures in a tooth stub, and a magazine sleeve retaining the dental pin such that only one complete pin section projects from the magazine sleeve at a time, and comprising ejection means for sequential ejection of the next successive pin section as each pin section is sheared off, wherein each pin section comprises a threaded cylindrical pin and an enlarged shaped head, the interior of the magazine sleeve having a matingly shaped chamber for permitting relative axial movement between the pin sections and the magazine sleeve while preventing rotational movement there between, and wherein said enlarged head includes an annular groove, and said magazine sleeve includes an inwardly directed resilient finger for engaging said annular groove to permit indexed ejection of successive pin sections and for retaining the remaining pin sections secured within the magazine sleeve.

23. A dental pin system as in claim 22, wherein said pin at said annular grooves has a larger diameter than the pin at the threaded portions and the throat portions.

24. A dental pin system comprising a dental pin having a plurality of contiguous coaxial pin sections each separated from the adjacent pin section by a reduced diameter throat portion to permit successive shearing off of the sections for sequential insertion of the pin sections into respective apertures in a tooth stub, and a magazine sleeve retaining the dental pin such that only one complete pin section projects from the magazine sleeve at a time, and comprising ejection means for sequential ejection of the next successive pin section as each pin section is sheared off, wherein each pin section comprises an enlarged shaped head, the interior of the magazine sleeve having a matingly shaped chamber for permitting relative axial movement between the pin sections and the magazine sleeve while preventing rotational movement therebetween, and wherein said magazine sleeve comprises an elongated barrel member having an internal axial passageway through which the pin is ejected, said chamber forming at least a part of said passageway, and comprising a diametrically opposed pair of inwardly directed tabs struck from the barrel and extending into said passageway to engage the enlarged heads of the pin sections to provide one way axial movement of the pin sections through the passageway and wherein the enlarged heads comprise an annular groove, and comprising an inwardly projecting rib at the distal end of the tabs for resiliently engaging the annular grooves.

25. A dental pin assembly, comprising an elongated dental pin having coaxial multiple pin portions separated from each other by reduced diameter shear portions for permitting shearing off of pin sections sequentially upon rotational insertion of a pin section in a respective aperture in a tooth stub; a sleeve adapter for retaining the dental pin and controlling sequential ejection of successive pin sections into an operative position as each previous pin section rotationally shears off, and a shank for operatively receiving the sleeve into one end thereof, the opposing end of the shank having means for rotatingly driving the shank to thread an operatively positioned pin section into an aperture in the tooth stub.

26. A dental pin assembly as in claim 25, wherein said shank comprises a hollow receiver chamber for accommodating the dental pin internally of the shank.

27. A dental pin assembly as in claim 26, wherein the cross section of the receiving chamber is greater than the pin to permit swaying of the upper end of the pin within the chamber.

28. A dental pin assembly as in claim 27, wherein the knobs comprise latterly projecting stems and enlarged knob heads, said knob heads extending beyond the periphery of the shank to facilitate the insertion and removal of the sleeve from the shank.

29. A dental pin assembly as in claim 26, wherein the sleeve is barrel shaped, having upper and lower tapered ends to permit sway of the barrel in the receiving chamber.

30. A dental pin assembly as in claim 25, and comprising a pair of diametrically opposed slots axially extending along the shank from said one end thereof, and wherein said sleeve comprises a corresponding pair of diametrically opposed knobs received into said slots.

31. A dental pin assembly as in claim 30, wherein said slots are inverted L-shaped to provide a twist lock of the sleeve into the shank.

32. A dental pin assembly as in claim 31, wherein the slot comprises a restriction to require a forced insertion of the knobs into the slots.

33. A dental pin assembly as in claim 30, wherein the knobs are color coded to identify the size of the pin.

34. A dental pin assembly as in claim 25, wherein the distal end of said shank is enlarged to provide increased thickness to accommodate retention of said adapter.

35. A dental pin assembly as in claim 25, wherein said other end of said shank comprises a reduced diameter neck portion and a vertical flat section for driving insertion into a dental handpiece.

36. A dental pin assembly as in claim 25, and comprising a manual driver for receiving the other end of the shank for manual rotation of the dental pin.

37. A dental pin assembly as in claim 25, and comprising restraining means on said adapter for preventing complete ejection of the dental pin from the adapter.

38. A dental pin assembly as in claim 25, and comprising means for permitting axial movement of the pin with respect to the adapter while preventing rotational movement of the pin with respect to said adapter.

39. A dental pin assembly as in claim 25, wherein the other end of the shank forms a grip whereby the shank itself is used as a manual driving tool.

40. A dental pin assembly, comprising an elongated dental pin having coaxial multiple pin portions separated from each other by reduced diameter shear portions for permitting shearing off of pin sections sequentially upon insertion of a pin section in a respective aperture in a tooth stub; a sleeve adapter for retaining the dental pin and controlling sequential ejection of successive pin sections into an operative position as each previous pin section shears off, and a shank for operatively receiving the sleeve into one end thereof, the opposing end of the shank having means for rotatingly driving the shank to thread an operatively positioned pin section into an aperture in the tooth stub, and wherein each pin section comprises an enlarged head, and further comprising a manual tool for receiving the enlarged head for final rotational adjustment of the pin section into the tooth stub.

* * * * *